(12) United States Patent
Eromaki et al.

(10) Patent No.: US 11,158,289 B2
(45) Date of Patent: Oct. 26, 2021

(54) WEARABLE DEVICE AND METHOD THEREIN (71) Applicant: Huawei Technologies Co., Ltd., Shenzhen (CN)

(72) Inventors: Marko Eromaki, Tampere (FI); Lauri Jääskelä, Kista (SE); Harri Hakulinen, Helsinki (FI)

(73) Assignee: HUAWEI TECHNOLOGIES CO., LTD., Shenzhen (CN)

( * ) Notice: Subject to any disclaimer, the term of this patent is extended or adjusted under 35 U.S.C. 154(b) by 0 days.

(21) Appl. No.: 16/757,061

(22) PCT Filed: Oct. 20, 2017

(86) PCT No.: PCT/EP2017/076852
§ 371 (c)(1),
(2) Date: Apr. 17, 2020

(87) PCT Pub. No.: WO2019/076465
PCT Pub. Date: Apr. 25, 2019

(65) Prior Publication Data
US 2020/0251071 A1 Aug. 6, 2020

(51) Int. Cl.
G09G 5/00 (2006.01)
G09G 5/12 (2006.01)
(Continued)

(52) U.S. Cl.
CPC ............... G09G 5/12 (2013.01); G06F 3/012 (2013.01); G09G 3/003 (2013.01); G09G 5/14 (2013.01); G09G 2370/16 (2013.01)

(58) Field of Classification Search
CPC .......... G02B 27/017; G02B 2027/0163; G02B 27/01; G06F 3/011; G06F 3/012; G06F 3/0346; G06F 3/14; G06F 1/163; G06F 3/013; G06F 3/04815; H04N 13/344; H04N 13/398; H04N 13/194; H04N 13/332;
(Continued)

(56) References Cited

U.S. PATENT DOCUMENTS 5,808,802 A 9/1998 Hur
10,176,783 B2 1/2019 Travers et al.
(Continued)

FOREIGN PATENT DOCUMENTS

| CA | 2927046 A1 | 10/2017 |
| CN | 103995352 A | 8/2014 |
| CN | 105210145 A | 12/2015 |

Primary Examiner — Hau H Nguyen
(74) Attorney, Agent, or Firm — Conley Rose, P.C.

(57) ABSTRACT

In a wearable device, a master unit comprises a first display and a first processing circuitry, and a slave unit comprises a second display and a second processing circuitry. A method aims at outputting information in said displays. The method comprises acquiring a sensor signal from a sensor in the master unit; generating a synchronisation signal, based on the acquired sensor signal; transmitting the synchronisation signal from the first processing circuitry to the second processing circuitry; rendering information to be outputted in the first display, and in the second display based on the synchronisation signal; and outputting the information on the first display and the second display, respectively according to the synchronisation signal.

20 Claims, 7 Drawing Sheets (51) Int. Cl.
  *G06F 3/01* (2006.01)
  *G09G 3/00* (2006.01)
  *G09G 5/14* (2006.01)

(58) Field of Classification Search
  CPC ............ H04N 13/38; H04N 2013/0096; G06T 19/006; G06T 19/00; G06T 15/00; G06T 17/00; G09G 2370/16; G09G 5/12; A61M 2205/507
  See application file for complete search history.

(56) References Cited

U.S. PATENT DOCUMENTS

| | | |
|---|---|---|
| 2003/0137528 A1 | 7/2003 | Wasserman et al. |
| 2011/0175903 A1 | 7/2011 | Munro et al. |
| 2013/0278631 A1* | 10/2013 | Border .................. G02C 5/143 345/633 |
| 2015/0185483 A1 | 7/2015 | Hiraide |
| 2015/0363979 A1* | 12/2015 | Takano .................. A61B 6/462 345/633 |
| 2016/0163283 A1 | 6/2016 | Chang et al. |

* cited by examiner

| x | y | z | xa | ya | za | time |
|---|---|---|----|----|----|------|
| 1 2 3 4 | 5 6 7 8 | 9 10 11 12 | 13 14 15 16 | 17 18 19 20 | 21 22 23 24 | 25 26 27 28 |

WEARABLE DEVICE AND METHOD THEREIN

CROSS-REFERENCE TO RELATED APPLICATIONS

This application is a National Stage of International Patent Application No. PCT/EP2017/076852 filed on Oct. 20, 2017, which is hereby incorporated by reference in its entirety.

TECHNICAL FIELD

Implementations described herein generally relate to a wearable device, and a method therein.

BACKGROUND

Augmented Reality (AR) and Virtual Reality (VR) are rapidly emerging technologies.

VR is a computer technology that uses a virtual reality headset to generate realistic images, sounds and other sensations that simulate a user's physical presence in a virtual or imaginary environment. A person using virtual reality equipment is able to "look around" the artificial world as he/she moves his/her head with the virtual reality equipment, and with high quality VR move about in it and possibly also interact with virtual features or items. The effect is commonly created by VR headsets comprising head-mounted goggles. VR is typically used for games and entertainment, but also for education, simulation and training purposes, etc.

AR is a live direct or indirect view of a physical, real-world environment whose elements are "augmented" by computer-generated or extracted real-world sensory input such as sound, video, graphics, GPS data, sensor data, etc. It is related to a more general concept called computer-mediated reality, in which a view of reality is modified (possibly even diminished rather than augmented) by a computer. AR enhances a user's current perception of reality, whereas in contrast, VR replaces the real world with a simulated imaginary environment. Augmentation techniques are typically performed in real time and in semantic context with environmental elements, such as overlaying supplemental information like for example the remaining time (and/or destination) to the next bus when the user is standing at a bus stop. Another example may be an AR device for construction workers which display information about the construction site.

A wearable device is designed for outputting three dimensional (3D) information, either AR or VR. However the existing wearable device has a construction with multiple connections to each display puts so that the wearable device becomes aesthetically awkward, and also heavy.

SUMMARY

It is therefore an objective to obviate at least some of the above mentioned disadvantages and to provide an improved wearable device for image output.

This and other objectives are achieved by the features of the appended independent claims. Further implementation forms are apparent from the dependent claims, the description and the figures.

According to a first aspect, a wearable device comprising a master unit and at least one slave unit is provided. The master unit comprises a first display and a first processing circuitry, and the slave unit comprises a second display and a second processing circuitry. The wearable device aims at outputting information in the first and second displays. The first processing circuitry is configured to acquire at least one sensor signal from a sensor comprised in the master unit. Further, the first processing circuitry is configured to generate a synchronisation signal, based on the acquired sensor signal. In addition, the first processing circuitry is also configured to transmit the generated synchronisation signal to the slave unit. Also, the first processing circuitry is configured to render information to be outputted in the first display. The first processing circuitry is furthermore configured to transmit the rendered information to the first display for outputting the rendered information on the first display. The second processing circuitry is configured to receive the synchronisation signal from the master unit. Further, the second processing circuitry is configured to render information to be outputted in the second display, based on the received synchronisation signal. The second processing circuitry is also configured to transmit the rendered information to the second display, for outputting the rendered information on the second display.

By using a separate processing circuitry for each display and render information to be outputted independently by the respective processing circuitries, yet based on the synchronisation signal, it is avoided to use heavy multi-wire based connections between a single processing circuitry and the displays as according to conventional solutions. In the previously known solutions, these connections between the processing circuitry and the displays comprises approximately 40-50 copper wires for each connection, having a considerable weight and volume. Thereby, an extended design freedom is provided, enabling construction of a wearable device being comfortable, convenient and attractive to wear for a user.

According to a first possible implementation of the wearable device according to the first aspect, the outputted information comprises three dimensional information. Further, the three dimensional information to be rendered is comprised both in the master unit, and in the slave unit.

By keeping the three dimensional information both in the master unit and in the slave unit, less information has to be exchanged between the respective processing circuitries, making it possible to use a low bandwidth connection between the master unit and the slave unit. Thereby low power consumption is required, leading to that a lighter battery, or batteries may be used, further reducing weight of the wearable device and also providing further design freedom. Further, as only very little information has to be exchanged, data transmission takes only a short time which enables low latency and reduces parallax problems between the images displayed on master and slave displays. Thereby, a better user experience is achieved.

According to a second possible implementation of the wearable device according to the first aspect, or according to the first possible implementation thereof, the first processing circuitry may be further configured to transmit the generated synchronisation signal to the slave unit via a low bandwidth connection.

Thanks to the low bandwidth connection, no high-bandwidth video link is required to be physically routed between the modules with cables. Thereby a very lightweight and convenient wearable device is achieved. Also, the low bandwidth connection requires low energy consumption, which puts reduced requirements on the batteries. Smaller/lighter batteries may then be used, leading to a yet lighter wearable device.

According to a third possible implementation of the wearable device according to the first aspect, or any previously described implementation thereof, the first processing circuitry may be further configured to transmit the generated synchronisation signal to the slave unit via a wireless communication interface.

Thanks to the wireless communication interface, further enhanced design freedom is achieved, as no physical cables has to be arranged between the master unit and the slave unit. Thereby, weight of the wearable device is also further reduced.

According to a fourth possible implementation of the wearable device according to the first aspect, or any previously described implementation thereof, the first processing circuitry may be further configured to transmit the generated synchronisation signal to the slave unit via a wired communication interface.

Thanks to the wired communication interface, a secure and reliable, yet rather lightweight communication interface between the master unit and the slave unit is provided.

According to a fifth possible implementation of the wearable device according to the first aspect, or any previously described implementation thereof, the first processing circuitry may be further configured to generate and transmit a synchronisation signal comprising a global time reference and sensor data, based on the acquired sensor signal.

By reducing the amount of data that has to be exchanged, the synchronisation may be made in short time, leading to low latency with low bandwidth, which also leads to low power usage. Thereby, the size of the power source may be reduced, leading to increased design freedom and less weight giving ergonomic advantages. Alternatively, the interval between battery charge may be extended, leading to enhanced user usefulness.

According to a sixth possible implementation of the wearable device according to the first aspect, or any previously described implementation thereof, the sensor comprised in the master unit may comprise any one of: a gyroscope, an accelerometer, and/or a magnetometer.

By having only one set of sensors in the master unit and share the obtained sensor data with the slave unit, problems with sensor drift is avoided, in comparison with having distinct sets of sensors in the master unit and the slave unit.

According to a seventh possible implementation of the wearable device according to the first aspect, or any previously described implementation thereof, the wearable device may comprise one master unit and a plurality of slave units, wherein each slave unit may comprise a display and a processing circuitry.

By providing several slave units, e.g. stacked onto each other in an array of displays, a richer and more convincing three dimensional viewing experience is achieved.

According to an eighth possible implementation of the wearable device according to the first aspect, or any previously described implementation thereof, the first processing circuitry is configured to render the three dimensional information from a first angle, and the second processing circuitry is configured to render the three dimensional information from a second angle, distinct from the first angle, in order to achieve a stereo effect for a user, at the first and second displays.

The distinct rendering of the respective images for the three dimensional scene at the processing circuitries, it is avoided to use a high-bandwidth video link for distributing information rendered at one common processing circuitry. Thereby weight is saved, and more flexibility is provided, when it comes to design of the wearable device.

According to a ninth possible implementation of the wearable device according to the first aspect, or any previously described implementation thereof, the master unit and the slave unit, each may comprise a separate memory.

Thanks to the separate memories of the master unit and the slave unit respectively, certain information such as knowledge of the three dimensional information to be rendered may be kept at the respective separate memories. Thereby, less information such as e.g. only position and location of the camera in the three dimensional space has to be communicated between the master unit and the slave unit. Thus low bandwidth content synchronisation is facilitated.

According to a tenth possible implementation of the wearable device according to the first aspect, or any previously described implementation thereof, the wearable device comprises a pair of eyeglasses.

Thereby a convenient embodiment of the wearable device is implemented.

According to an eleventh possible implementation of the wearable device according to the first aspect, or any previously described implementation thereof, the wearable device comprises a headwear, and wherein the first display and the second display are arranged in association with the respective eye positions of the user.

Thereby an alternative embodiment of the wearable device is implemented.

According to a twelfth possible implementation of the wearable device according to the first aspect, or any previously described implementation thereof, the rendered information comprises any of augmented reality, or virtual reality.

Thereby, the rendered information is further specified.

According to a second aspect, a method in a wearable device according to the first aspect, or any previously described implementation thereof, is provided, wherein the wearable device comprises a master unit and at least one slave unit. The master unit comprises a first display and a first processing circuitry, and the slave unit comprises a second display and a second processing circuitry. The method aims at outputting information in the first display and the second display. The method comprises acquiring, by the first processing circuitry, at least one sensor signal from a sensor comprised in the master unit. Further, the method also comprises generating, by the first processing circuitry, a synchronisation signal, based on the acquired sensor signal. Also, the method in addition comprises transmitting the generated synchronisation signal from the first processing circuitry to the second processing circuitry. The method furthermore comprises rendering information to be outputted in the first display at the master unit, and in the second display at the slave unit, based on the synchronisation signal. The method also comprises outputting the rendered information on the first display and the second display, respectively according to the transmitted synchronisation signal.

The advantages of the method according to the second aspect, and the implementations thereof, are the same as has been described for the wearable device of the first aspect, and the corresponding implementations thereof.

According to a first possible implementation of the method according to the second aspect, the outputted information comprises three dimensional information. Further, the three dimensional information to be rendered is comprised both in the master unit, and in the slave unit.

According to a second possible implementation of the method according to the second aspect, or according to the first possible implementation thereof, the transmission of the generated synchronisation signal from the first processing circuitry in the master unit, to the slave unit may be made via a low bandwidth connection.

According to a third possible implementation of the method according to the second aspect, or any previously described implementation thereof, the transmission of the generated synchronisation signal from the first processing circuitry in the master unit, to the slave unit may be made via a wireless communication interface.

According to a fourth possible implementation of the method according to the second aspect, or any previously described implementation thereof, the transmission of the generated synchronisation signal from the first processing circuitry in the master unit, to the slave unit may be made via a wired communication interface.

According to a fifth possible implementation of the method according to the second aspect, or any previously described implementation thereof, the generation and transmission of the synchronisation signal comprising a global time reference and sensor data may be based on the acquired sensor signal.

According to a sixth possible implementation of the method according to the second aspect, or any previously described implementation thereof, the generation and transmission of the synchronisation signal by the first processing circuitry in the master unit may comprise sensor signals generated by at least one of: a gyroscope, an accelerometer, and/or a magnetometer.

According to a seventh possible implementation of the method according to the second aspect, or any previously described implementation thereof, the generation and transmission of the synchronisation signal may be made by the first processing circuitry in the master unit, to a plurality of slave units, wherein each slave unit may comprise a display and a processing circuitry.

According to an eighth possible implementation of the method according to the second aspect, or any previously described implementation thereof, the first processing circuitry is configured to render the three dimensional information from a first angle, and the second processing circuitry is configured to render the three dimensional information from a second angle, distinct from the first angle, in order to achieve a stereo effect for a user, at the first and second displays.

According to a ninth possible implementation of the method according to the second aspect, or any previously described implementation thereof, the master unit and the slave unit, each may comprise a separate memory.

According to a tenth possible implementation of the method according to the second aspect, or any previously described implementation thereof, the wearable device comprises a pair of eyeglasses.

According to an eleventh possible implementation of the method according to the second aspect, or any previously described implementation thereof, the wearable device comprises a headwear, wherein the first display and the second display are arranged in association with the respective eye positions of the user.

According to a twelfth possible implementation of the method according to the second aspect, or any previously described implementation thereof, the rendered information comprises any of augmented reality, or virtual reality.

According to a third aspect, a computer program is provided, comprising program code for performing a method, according to the second aspect, or any previously described implementation thereof, when the computer program runs on a computer.

Other objects, advantages and novel features of the aspects of the invention will become apparent from the following detailed description.

BRIEF DESCRIPTION OF THE DRAWINGS

Various embodiments are described in more detail with reference to attached drawings, illustrating examples of embodiments of the invention in which.

DETAILED DESCRIPTION

Embodiments of the invention described herein are defined as a wearable device, and a method therein, which may be put into practice in the embodiments described below. These embodiments may, however, be exemplified and realised in many different forms and are not to be limited to the examples set forth herein; rather, these illustrative examples of embodiments are provided so that this disclosure will be thorough and complete.

Still other objects and features may become apparent from the following detailed description, considered in conjunction with the accompanying drawings. It is to be understood, however, that the drawings are designed solely for purposes of illustration and not as a definition of the limits of the herein disclosed embodiments, for which reference is to be made to the appended claims. Further, the drawings are not necessarily drawn to scale and, unless otherwise indicated, they are merely intended to conceptually illustrate the structures and procedures described herein.

Figure 1A:
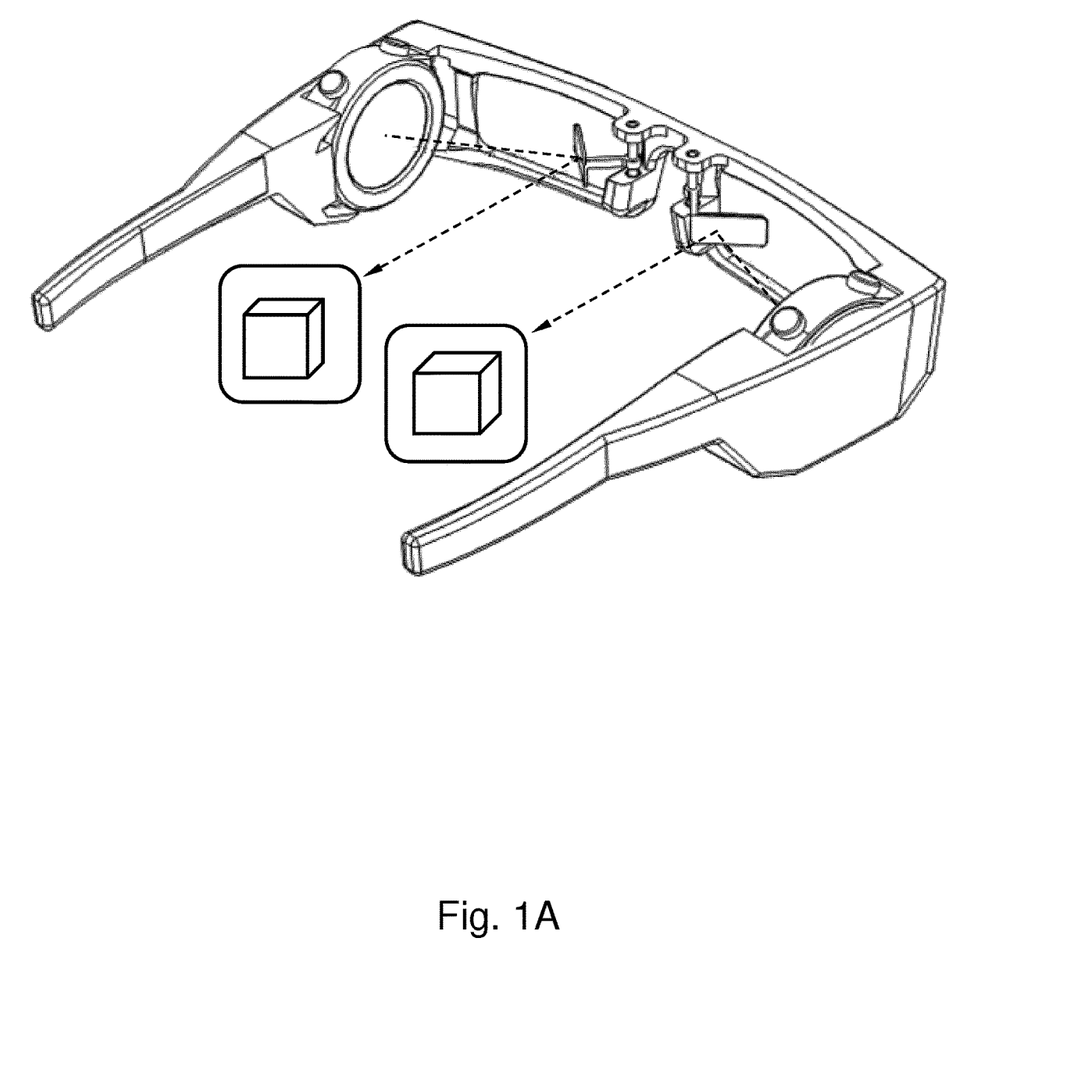
FIG. 1A is a schematical illustration of a wearable device.

A wearable device for outputting three dimensional (3D) information, either AR or VR, may comprise a pair of stereo AR/VR glasses, as illustrated in FIG. 1A. There is one separate display dedicated for each eye of the user, and the rendered respective 3D images are synchronised and slightly displaced in relation to each other in order to achieve the 3D effect.

Figure 1B:
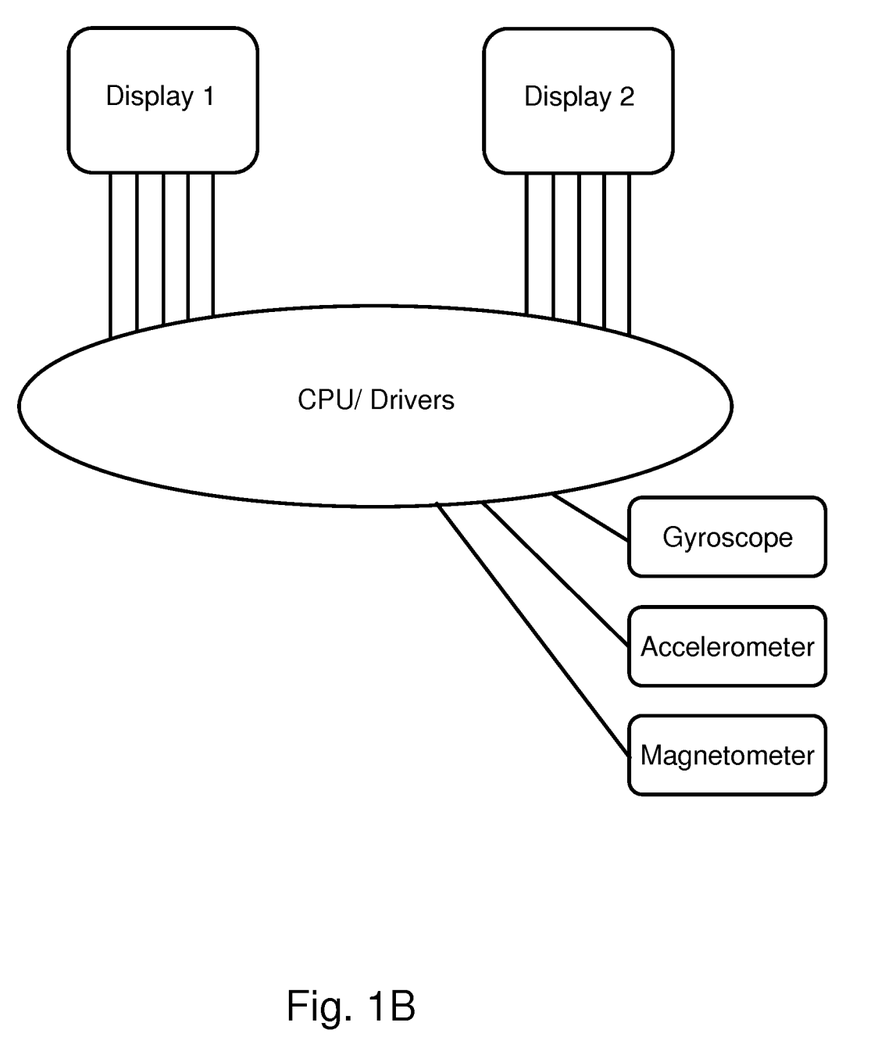
FIG. 1B is a block diagram illustrating a wearable device.

A schematic presentation of the stereo AR/VR glasses of FIG. 1A is presented in FIG. 1B. A processor may be connected to various sensors such as e.g. a gyroscope, an accelerometer and a magnetometer. Further, the respective displays are connected to the common processor via multiple connections, e.g. 40-50 wires to each display. The processor may thereby render and synchronise the images to be outputted to the user. However, the conventional headset construction with multiple connections to each display puts severe limitations on the design of the wearable headset. The result is that the wearable device becomes aesthetically awkward, and also heavy. As most people who sometime has carried a pair of glasses of any arbitrary kind knows, also a small increase in weigh adds a substantial user discomfort, in particular when carried over a long period of time. Stereo AR/VR glasses are typically so heavy that they present an ergonomic hazard to the user when worn for any substantial amount of time. They are typically also clumsy and limits the user's physical movements.

It would for these reasons be desired to produce a wearable device which offers a greater freedom when it comes to design issues and/or has less weight while still being able to render and synchronise output of 3D images.

Figure 2:
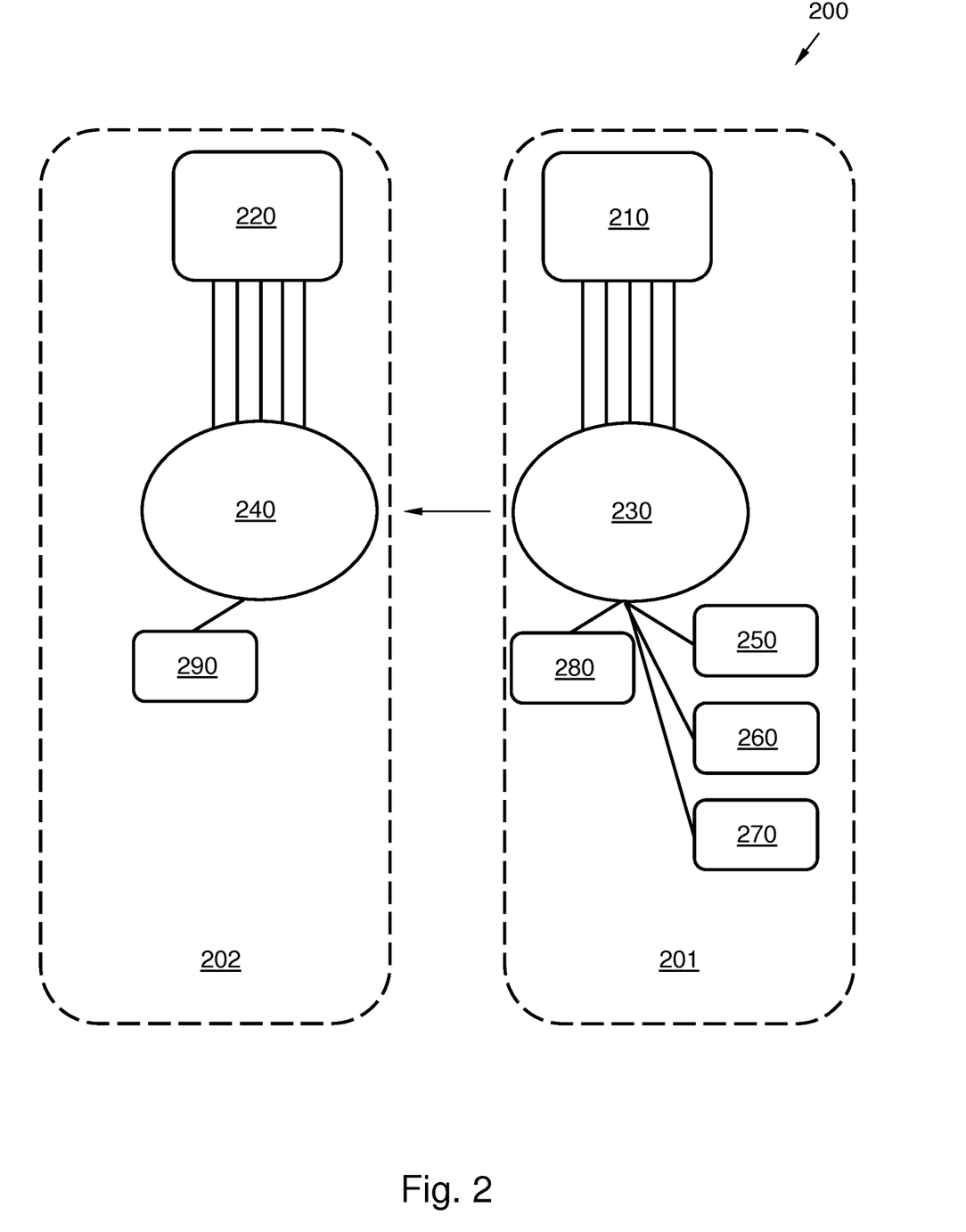
FIG. 2 is a block diagram illustrating a wearable device according to an embodiment.

FIG. 2 is a schematic illustration over a wearable device 200. The wearable device 200 may comprise a pair of stereo AR/VR glasses, a helmet, or other similar headgear or headwear for outputting AR/VR information to a user. The wearable device 200 may also be referred to as smart glasses, wearable computer glasses, smart lenses, smart binoculars, face-guard, smart goggles, sun glasses, diving masks, welding masks, etc.

The wearable device 200 comprises a master unit 201 and a slave unit 202. The master unit 201 comprises a first display 210 and a first processing circuitry 230, while the slave unit 202 comprises a second display 220 and a second processing circuitry 240. The master unit 201 also comprises one or several sensors such as a gyroscope 250, an accelerometer 260 and/or a magnetometer 270. The first display 210 and the second display 220 may comprise e.g. an Optical Head-Mounted Display (OHMD), which is a wearable device that has the capability of reflecting projected images as well as allowing the user to see through it, in an augmented reality implementation. In some other embodiments, the displays 210, 220 may comprise embedded wireless glasses with transparent Heads-Up Display (HUD) or AR overlay that has the capability of reflecting projected digital images as well as allowing the user to see through it, or even see better with it (by added correctional lenses and/or sun shades etc.).

The outputted information of the first display 210 and the second display 220 may be projected on the respective display 210, 220 by a respective projector in the master device 201 and the slave device 202 in some embodiments.

For enhanced clarity, any internal electronics or other components of the wearable device 200, not completely indispensable for understanding the herein described embodiments have been omitted from FIG. 2.

The first processing circuitry 230 and/or the second processing circuitry 240 may, respectively, comprise one or more instances of a processing circuit, i.e. a Central Processing Unit (CPU), a processing unit, a processor, an Application Specific Integrated Circuit (ASIC), a microprocessor, or other processing logic that may interpret and execute instructions. The herein utilised expression "processing circuitry" may thus represent a plurality of processing circuits, such as, e.g., any, some or all of the ones enumerated above.

In some embodiments, the master unit 201 may comprise a first memory 280 and the slave unit 202 may comprise a second memory 290 which is distinct from the first memory 280.

The first memory 280 and/or the second memory 290 may comprise a respective physical device utilised to store data or programs, i.e., three dimensional information and sequences of instructions, on a temporary or permanent basis. According to some embodiments, the memories 280, 290 may comprise integrated circuits comprising silicon-based transistors. Further, the memories 280, 290 may be volatile or non-volatile.

In some embodiments, the respective first memory 280 and/or the second memory 290 may both comprise common information concerning three dimensional information to be rendered in the first display 210 and the second display 220, respectively. The three dimensional information may comprise a VR universe in some embodiments when the wearable device 200 is dedicated for VR. The VR universe may for example comprise a room, a building or other structure within which the user may "move around" when using the wearable device 200.

In other embodiments, wherein the wearable device 200 is dedicated for AR, the three dimensional information may comprise AR information, which then is outputted in the displays 210, 220, overlaid to the real world information. The AR information may be associated with an object or a geographical position of the user's perceived real world wherein the user is situated. Some arbitrary examples of AR information may be graphics, text, documents, images, video, and/or various sensor data such as e.g. time, temperature, etc., depending on application of the wearable device 200. In case the wearable device 200 is utilised on a construction site, the AR information may comprise blue prints, drawings, construction specifications etc., relevant for the particular construction site according to the instantaneous view and position of the user (or in fact, rather the wearable device 200).

The three dimensional information comprising all the universe (AR or VR) which is to be rendered and outputted on the respective displays 210, 220 may be comprised in both the respective first memory 280 (in the master unit 201) and the second memory 290 (in the slave unit 202).

Thereby, this information does not have to be transmitted from the master unit 201 to the slave unit 202, thereby enabling a low bandwidth connection between the master unit 201 and the slave unit 202. Thereby only a power consumption lower than a threshold limit is required, leading to that a smaller/lighter battery, or batteries may be used, further reducing weight of the wearable device and also providing further design freedom. Further, as only very little information has to be exchanged between the master unit 201 and the slave unit 202, data transmission takes only a short time which enables low latency and reduces parallax problems between the images displayed on master and slave displays. Thereby, a better user experience is achieved.

The wearable device 200 thus comprises separate wireless processing and display modules 210, 220 for the respective (right/left) eyes of the user, each rendering the view independently, however based on a synchronisation signal.

The synchronisation signal serves the purpose of synchronising the outputted view on the first display 210 in the master unit 201 with the outputted view on the second display 220 in the slave unit 202, in time and/or in space. The synchronisation signal may comprise a global time reference, for synchronising the first processing circuitry 230 with the second processing circuitry 240, in time.

Further, for synchronising the outputted view on the first display 210 in the master unit 201 with the outputted view on the second display 220 in the slave unit 202, in space, a sensor signal generated from one or several sensors in the master unit 201 may be comprised, enabling the first processing circuitry 230 and the second processing circuitry 240 to determine which segment of the three dimensional world stored in the respective memories 280, 290. Thus the sensor signal may comprise e.g. three orthogonal coordinates in a Cartesian coordinate system (for determining position of the user/wearable device 200), a sensor signal for determining direction of the wearable device 200 and sensor signals for determining lateral and/or horizontal tilting of the wearable device 200. In case the stored AR/VR universe is limited, e.g. always assuming that the user is standing while using the wearable device 200, the height coordinate may be set to a constant value and thereby does not have to be part of the synchronisation signal (arbitrary non-limiting example only, the space position reference may be realised in many different ways leading to the same result, depending on implementation).

In the illustrated embodiments, the master unit 201 and the slave unit 202 synchronise their renderings so that they both render the same three dimensional information/scene but slightly displaced, i.e. at a slightly different angle. Thereby a stereoscopic pair of images may be rendered by the respective processing circuitries 230, 240 and outputted by the respective displays 210, 220 to achieve a stereo effect as perceived by the user. The difference between the presentational angles of the master unit 201 and the slave unit 202 may be predetermined and constant in some embodiments, for creating the stereo effect of the rendered image.

Because the eyes of humanoids, are located at different lateral positions on the head, binocular vision results in two slightly different images projected to the retinas of the eyes. The differences are mainly in the relative horizontal position of objects in the two images. These positional differences are referred to as horizontal disparities or, more generally, binocular disparities. Disparities are processed in the visual cortex of the brain to yield depth perception. While binocular disparities are naturally present when viewing a real world three dimensional scene with two eyes, they can also be simulated by artificially outputting two different images separately to each eye of the user at the respective displays 210, 220, using a method called stereoscopy, which may be applied in some embodiments. The perception of depth in the outputted information/image may also referred to as "stereoscopic depth".

Low latency of the synchronisation signal between the master unit 201 and the slave unit 202, i.e. a latency below a predetermined or configurable threshold limit, prevents parallax problems or animations being out of sync. A low bandwidth link for the synchronisation will facilitate wireless synchronisation, and also lead to low power consumption. However, in distinct alternative embodiments, a wired or wireless high bandwidth link may be used.

The connection between the first processing circuitry 230 of the master unit 201 and the second processing circuitry 240 of the slave unit 202 may with advantage be made via a low bandwidth connection. Thereby, power consumption may be kept low, resulting in that a smaller/lighter power source, such as e.g. one or several batteries, may be utilised, in comparison with the conventional solution. Thus, the total weight of the wearable device 200 may be reduced, leading to ergonomic advantages for the user. Low weight in combination with a design focusing on user ergonomics and/or attractive design are important issues for enhancing the wearability on an everyday basis, or long term basis, of the wearable device 200.

Alternatively, the same power source as in the conventional solution may be used, but with a longer operational time before recharging. The master unit 201 and the slave unit 202 may each have their own respective battery, or set of batteries in some embodiments. In other embodiments, the master unit 201 and the slave unit 202 may share the same battery, or set of batteries.

The low bandwidth connection may be a wireless connection in some embodiments, based on e.g. Bluetooth or other similar wireless communication protocol for short range transmission of wireless communication, e.g. Near Field Communication (NFC), Radio-Frequency Identification (RFID), Z-wave, ZigBee, IPv6 over Low power Wireless Personal Area Networks (6LoWPAN), Wireless Highway Addressable Remote Transducer (HART) Protocol, Wireless Universal Serial Bus (USB), optical communication such as Infrared Data Association (IrDA), Low-Power Wide-Area Network (LPWAN) such as e.g. LoRa, etc.; to name but a few possible examples of wireless communications in some different embodiments.

An advantage with wireless communication between the first processing circuitry 230 of the master unit 201 and the second processing circuitry 240 of the slave unit 202, possibly via a respective wireless transceiver (or alternatively a wireless transmitter in the master unit 201 and a wireless receiver in the slave unit 202), is that no connecting cables are required, again saving some weight, but perhaps more important provide a greater freedom when designing the wearable device 200. The processing circuitries 230, 240 may, thanks to the wireless communication, for example be positioned several centimetres/decimetres from the respective displays 210, 220; and may not necessarily be comprised in the same physical entity as the displays 210, 220 (although comprised in the same logical entity as illustrated in FIG. 2). In case the wearable device 200 comprises a helmet, hat or other similar headwear, the processing circuitries 230, 240 may be comprised for example on the back or on top of the headwear, in some alternative embodiments, which may provide design advantages and/or ergonomic advantages.

The low bandwidth connection may alternatively be a wired connection in some embodiments using e.g. Inter-Integrated Circuit (I2C), or similar communication bus, such as e.g. ACCESS.bus (A.b), the Video Electronics Standards Association (VESA) Display Data Channel (DDC) interface, the System Management Bus (SMBus), Power Management Bus (PMBus), the Intelligent Platform Management Bus (IPMB), Two-Wire Interface (TWI), Two-Wire Serial Interface (TWSI), etc. The wired low bandwidth connection make use of 2-3 wires. The wired connection may have an advantage of providing a stable connection, not requiring a pairing and bonding procedure as may be the case with e.g. a Bluetooth connection. A wired connection may also be more secure than a wireless connection as, at least some wireless communication protocols such as e.g. Bluetooth may have a weakness for various security attacks, such as bluejacking, bluesnarfing, and/or bluebugging.

According to certain embodiments, a synchronisation method is defined, enabling synchronisation of the image rendered (independently, however based on the synchronisation signal) on the first display 210 and on the second display 220, respectively. In order to achieve low power consumption and also low bandwidth communication, only the device position and global time signal may be synchronised in some embodiments.

Thereby, to achieve low latency and low bandwidth synchronisation, the wearable device 200 comprises one master unit 201 and one, or several, slave units 202. The master unit 201 may comprise one or several sensors of the same or different types, such as e.g. the gyroscope 250, the accelerometer 260 and/or the magnetometer 270 to place and rotate a camera in a 3D world. Information such as e.g. camera position, rotation and animation synchronisation signal may be sent to the slave unit 202, which uses this data to render the same scene at the second display 220, as rendered by the first processing circuitry 230 at the first display 210. Thus, the slave unit 202 may not comprise any own sensors; or at least not use any own sensor data. Thereby, both the master unit 201 and the slave unit 202 may render the same scene, possibly outputted at different view angles to create a stereo view effect of the user, without experience any problems with e.g. sensor drift between the respective units 201, 202.

The provided solution provides advantages regarding the wearable device mechanics and industrial design. Thanks to the increased design flexibility and reduced weight of the wearable device 200, a very lightweight and casual "smart glass" frames are provided, since no high-bandwidth video link needs to be physically routed between the modules with cables. Further, low power consumption saves battery, leading to a yet lighter wearable device 200. Thereby, a convenient and comfortable wearable device 200 is achieved, which may be carried effortlessly by the user, continuously or for a long period of time.

The head of the user is typically most sensible for excessive weight on the rather limited parts of the head that are supporting an eyewear, i.e. the root of the nose and the upper parts of the ears, why also a modest weight reduction will result in increased ergonomic user experience. The user will be able to carry the wearable device 200 for a longer period of time, with less discomfort; possibly the wearable device 200 may be used on an everyday basis in some embodiments.

Figure 3:
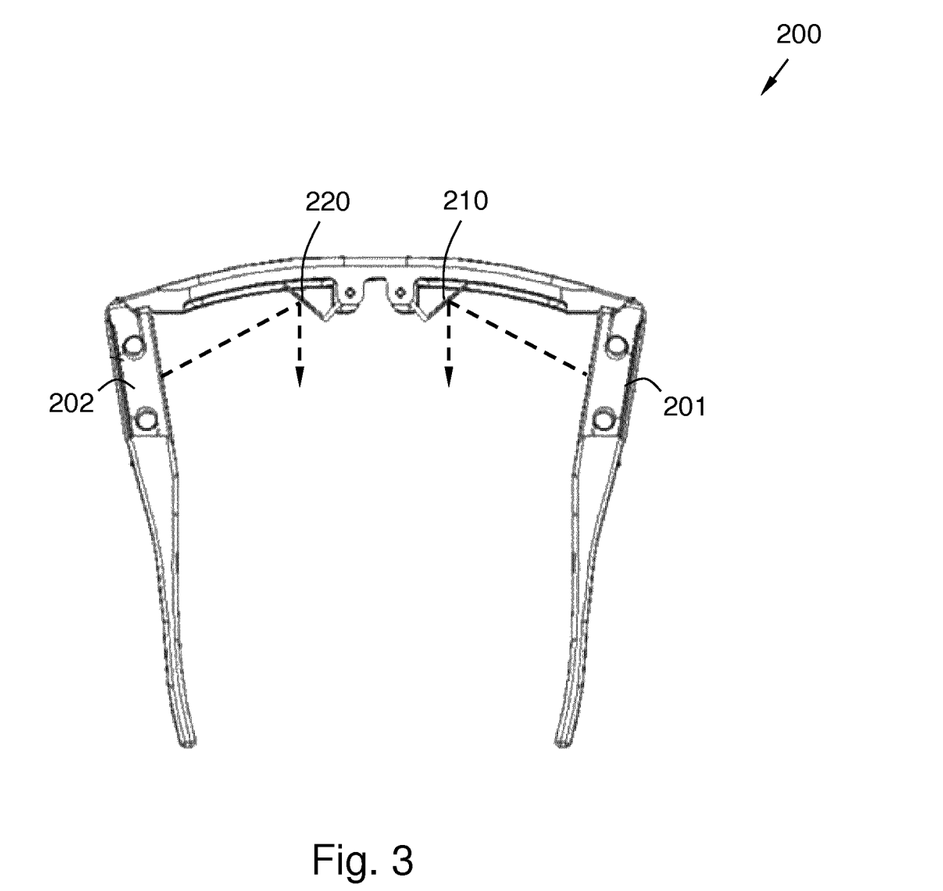
FIG. 3 is a block diagram illustrating a wearable device according to an embodiment.

FIG. 3 presents an example of a design of a wearable device 200, e.g. as previously schematically illustrated in FIG. 2 and described above, comprising a pair of stereo AR/VR glasses.

Each of the master unit 201 and the slave unit 202 render a respective image, based on the common synchronisation signal, which may comprise a global time reference and sensor data achieved from sensors 250, 260, 270 of the master unit 201. Further, three dimensional information to be rendered may be comprised both in the first memory 280 of the master unit 201, and in the second memory 290 of the slave unit 202, leading to that less information has to be transferred between the master unit 201 and the slave unit 202, which results in low latency. The purpose of the synchronisation signal is to synchronise the output of the respectively rendered information, made on the first display 210 and the second display 220.

As briefly mentioned previously, the wearable device 200 may comprise a plurality of slave units 202, each comprising one separate display and processing circuitry. The respective displays of these slave units 202 may be stacked onto each other in some embodiments. The stacked displays may be completely or partially transparent in some embodiments. Thereby, an enhanced three dimensional effect may be created.

Figure 4:
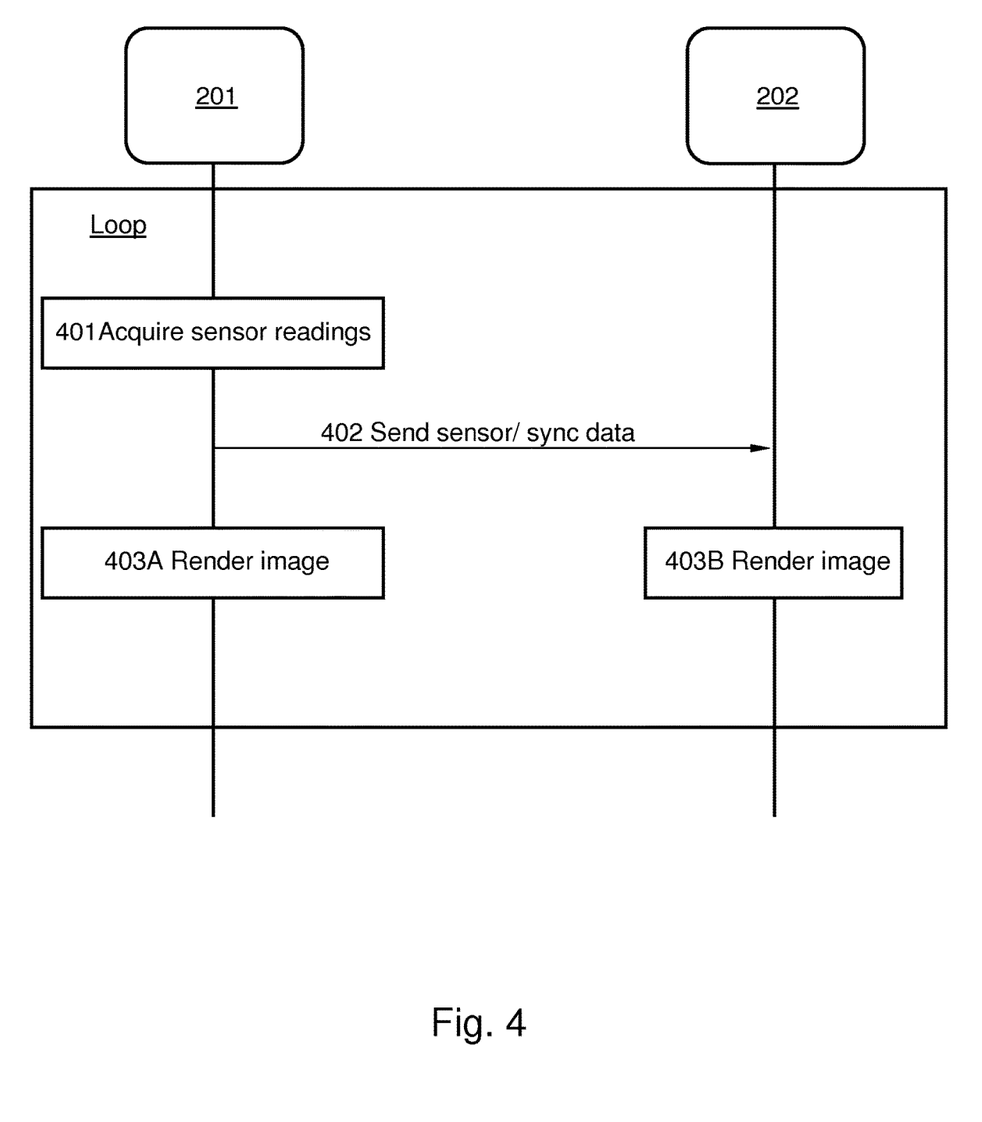
FIG. 4 is a flow chart illustrating an embodiment of a method in a wearable device.

FIG. 4 illustrates an example of a method for outputting information in the first and second displays 210, 220 of the wearable device 200.

For each frame, the master unit 201 may update at least any or some of its sensor values, such as e.g. any of an accelerometer value, a gyroscope value, an accelerometer value, a device position, a camera position, a position reference, a rotation and animation synchronisation reference, etc., in a first method step 401, and send them along with a global time reference signal to be received by the slave unit 202 in a subsequent step 402. The global time reference signal may be generated by a time measuring device of the master unit 201. After the data is sent, the master unit 201 may render the image and output it on the first display 210, based on the sensor data in step 403A. When the slave unit 202 receives the synchronisation signal comprising the sensor data, it will also render the image on the second display 220 in step 403B, based on the synchronisation signal. Since the amount of data is very small, the data transmission of the data takes a very short time, which enables low latency and reduces parallax problems between the images displayed on the first display 210 of the master unit 201, and the second display 220 of the slave unit 202.

Figure 5:
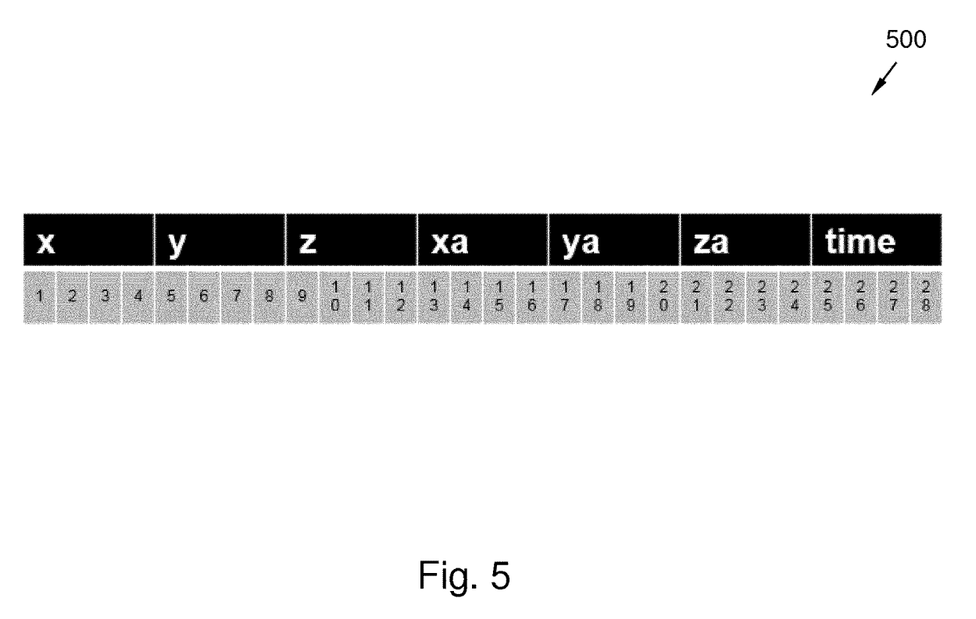
FIG. 5 is a block diagram illustrating encodings of data points in a synchronisation frame.

FIG. 5 is a block diagram illustrating encodings of data points in a synchronisation frame 500. If the all of the data points are encoded as 32-bit values, the size of one synchronisation frame can be encoded into 28 bytes, according to an implementation embodiment.

Bandwidth <<100 bytes per frame (e.g. every 16 ms at 60 Hz) may be achieved with practically any wireless technology. For example, Bluetooth 2.0 provides max 2.1 Mbit/s bandwidth, leading to transmit time of 28*8/2100000~=0.1 ms for one frame, enabling low latency with low bandwidth (and therefore low power usage).

Figure 6:
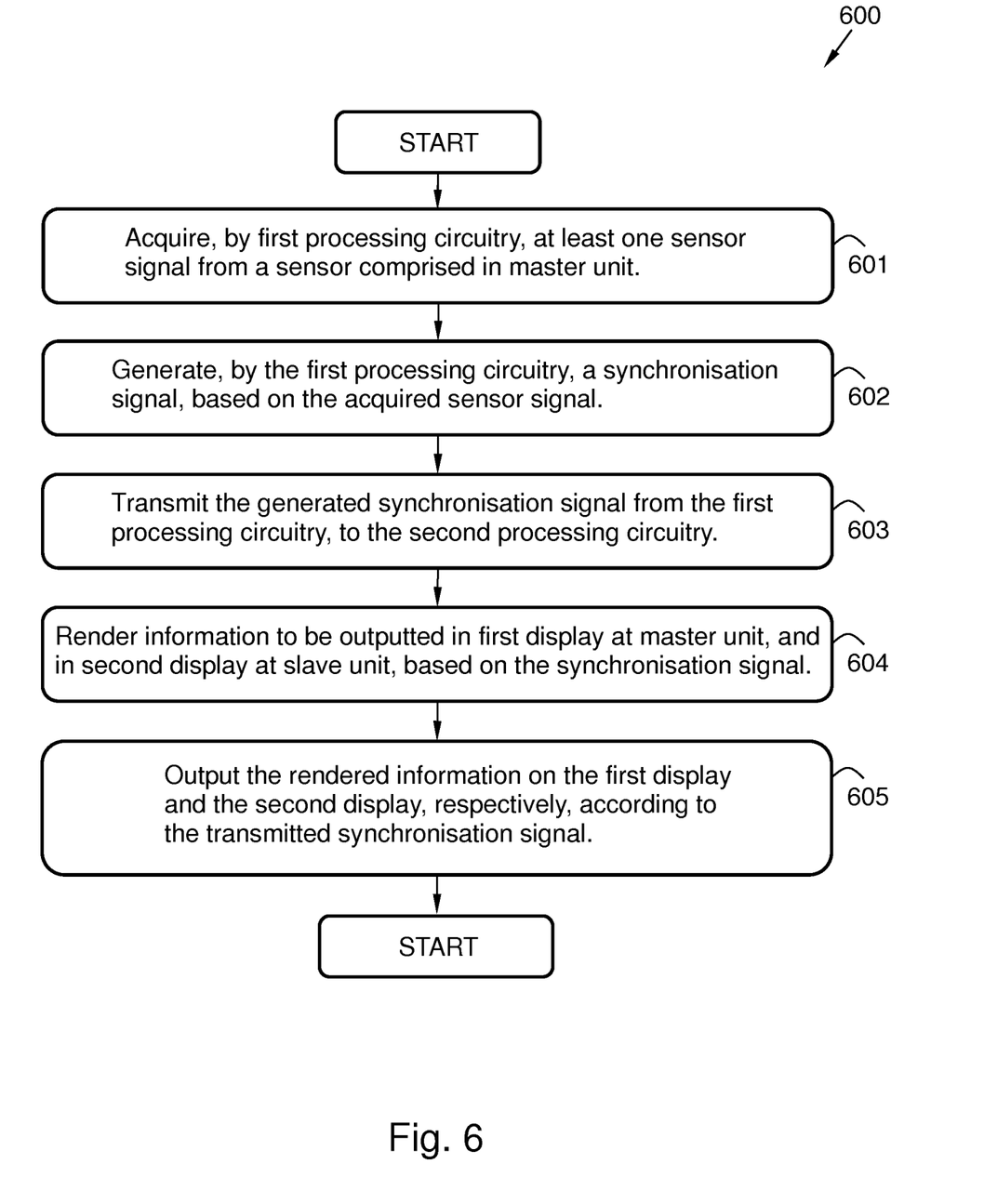
FIG. 6 is a flow chart illustrating a method in a wearable device according to an embodiment of the invention.

FIG. 6 is a flow chart illustrating an embodiment of a method 600 in a wearable device 200 comprising a master unit 201 and at least one slave unit 202. The master unit 201 comprises a first display 210 and a first processing circuitry 230, while the slave unit 202 comprises a second display 220 and a second processing circuitry 240, for outputting information in the first and second displays 210, 220.

The information to be outputted may comprise three dimensional information in some embodiments, such as a three dimensional scenario. Further, the outputted information may comprise augmented reality information, or mediated reality information in some embodiments. In other embodiments, the outputted information may comprise virtually reality information. The three dimensional information to be rendered may be comprised both in the master unit 201, and in the slave unit 202, e.g. in order to achieve a stereo effect for a user, at the first and second displays 210, 220.

The wearable device 200 may comprise a pair of eyeglasses in some embodiments. In other embodiments, the wearable device 200 may comprise a headwear, and wherein the first display 210 and the second display 220 are arranged in association with the respective eye positions of the user.

To appropriately render and output information in the displays 210, 220, the method 600 may comprise a number of steps 601-605. It is however to be noted that any, some or all of the described steps 601-605, may be performed in a somewhat different chronological order than the enumeration indicates, be performed simultaneously or even be performed in a completely reversed order according to different embodiments. Some actions may be performed within some, but not necessarily all embodiments. Further, it is to be noted that some actions may be performed in a plurality of alternative manners according to different embodiments, and that some such alternative manners may be performed only within some, but not necessarily all embodiments.

The wearable device 200 may in some embodiments periodically re-perform any, some or all of step 601-605, thereby enabling output of information in the first and second displays 210, 220 continuously. The method 600 may comprise the following steps:

Step 601 comprises acquiring, by the first processing circuitry 230, at least one sensor signal from a sensor 250, 260, 270, comprised in the master unit 201.

The sensor 250, 260, 270 may comprise e.g. a gyroscope 250, an accelerometer, a magnetometer 270, a camera, a solid state compass, a positioning device such as e.g. a Global Positioning System (GPS) device, etc.

Thus, the sensor signal may comprise sensor data acquired from any one, several or all of the enumerated sensors 250, 260, 270 in different embodiments. The sensor signal makes it possible for the first processing circuitry 230, and later also the second processing circuitry 240 in the slave device 202, to position the device 200 correctly in the three dimensional world which is rendered and to be outputted on the respective displays 210, 220. The sensor data thereby comprises a spatial reference enabling determination of information to be outputted.

Step 602 comprises generating, by the first processing circuitry 230, a synchronisation signal, based on the acquired 601 sensor signal.

The generated synchronisation signal may comprise a global time reference and sensor data (spatial reference), based on the acquired 601 sensor signal. The purpose of the spatial reference is to enable the second processing circuitry 240 in the slave device 202 to determine which subset of the information stored in the second memory 290 to be outputted on the second display 220, synchronised in position with the information to be outputted on the first display 210 of the master device 201.

The global time reference may be generated by a time measuring device comprised in the master device 201 in some embodiments. Thereby, a synchronisation in time of the outputted information, outputted in the first display 210 and the second display 220, respectively, thereby providing an illusion of the user to move around in the three dimensional AR/VR universe, as the wearable device 200 is displaced.

In some embodiments, the generated synchronisation signal may comprise device position and the global time reference. In some other embodiments, the generated synchronisation signal may comprise sensor/camera position, rotation and animation synchronisation signal. In yet some embodiments, the synchronisation signal may comprise accelerometer and gyroscope values along with the global time reference.

Step 603 comprises transmitting the generated 602 synchronisation signal from the first processing circuitry 230 of the master device 201 to the second processing circuitry 240 of the slave device 202.

The transmission of the generated synchronisation signal to the slave unit 202 may be made via a low bandwidth connection, i.e. a bandwidth lower than a predefined or configurable threshold limit such as e.g. approximately 56 kbit/s; 100 kbit/s; «100 bytes per frame (e.g. every 16 ms at 60 Hz); 2.1 Mbit/s, etc., or there about, in different embodiments. In some embodiments, the low bandwidth connection may comprise a wireless communication interface; or alternatively a wired communication interface.

Step 604 comprises rendering information to be outputted in the first display 210 at the master unit 201, and in the second display 220 at the slave unit 202, based on the received synchronisation signal. The rendered information by the respective displays 210, 220 is thereby synchronised in time and in space.

In some embodiments, the rendered information of the first processing circuitry 230 may comprise the three dimensional information from a first angle while the rendered information of the second processing circuitry 240 may comprise the three dimensional information from a second angle, distinct from the first angle, in order to achieve a stereo effect for a user, at the first and second displays 210, 220 in some embodiments. The rendered respective three dimensional information thus may form a stereoscopic pair of images, slightly displaced in relation to each other, for creating or enhancing the illusion of depth in the image as perceived by the user.

Further, the three dimensional information to be rendered may be comprised both in a first memory 280 of the master unit 201, and in a second memory 290 of the slave unit 202, leading to that less information has to be transferred between the master unit 201 and the slave unit 202, which results in low latency.

Step 605 comprises outputting the rendered 604 information on the first display 210 and the second display 220, respectively, according to the transmitted 603 synchronisation signal.

At least a sub-set of the previously described method steps 601-605 to be performed in the wearable device 200 may be implemented through the first processing circuitry 230 in the master unit 201 and the second processing circuitry 240 in the slave unit 202, together with a computer program product for performing the functions of at least some of the method steps 601-605. Thus a computer program product, comprising instructions for performing the method steps 601-605 may output information in the first and second displays 210, 220, when the computer program is loaded into the processing circuitries 230, 240.

The computer program mentioned above may be provided for instance in the form of a data carrier carrying computer program code for performing at least some of the method steps 601-605 according to some embodiments when being loaded into the processing circuitries 230, 240. The data carrier may be, e.g., a hard disk, a CD ROM disc, a memory stick, an optical storage device, a magnetic storage device or any other appropriate medium such as a disk or tape that may hold machine readable data in a non-transitory manner. The computer program product may furthermore be provided as computer program code on a server and downloaded to the wearable device 200 remotely, e.g., over an Internet or an intranet connection.

In some embodiments, any, some or all method steps 601-605 may be iterated infinitely, for a limited period of time, or until a threshold limit is achieved.

The terminology used in the description of the embodiments as illustrated in the accompanying drawings is not intended to be limiting of the described wearable device 200, method 600 therein, and/or computer program. Various changes, substitutions and/or alterations may be made, without departing from the invention as defined by the appended claims.

As used herein, the term "and/or" comprises any and all combinations of one or more of the associated listed items. The term "or" as used herein, is to be interpreted as a mathematical OR, i.e., as an inclusive disjunction; not as a mathematical exclusive OR (XOR), unless expressly stated otherwise. In addition, the singular forms "a", "an" and "the" are to be interpreted as "at least one", thus also possibly comprising a plurality of entities of the same kind, unless expressly stated otherwise. It will be further understood that the terms "includes", "comprises", "including" and/or "comprising", specifies the presence of stated features, actions, integers, steps, operations, elements, and/or components, but do not preclude the presence or addition of one or more other features, actions, integers, steps, operations, elements, components, and/or groups thereof. A single unit such as e.g. a processor may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms such as via Internet or other wired or wireless communication system.

Finally, it should be understood that the present invention is not limited to the embodiments described above, but also relates to and incorporates all embodiments within the scope of the appended independent claims.

The invention claimed is:

1. A wearable device comprising:
a master unit comprising a first display, a first processing circuitry coupled to the first display, and a sensor coupled to the first processing circuitry; and
a slave unit coupled to the master unit and comprising a second display and a second processing circuitry coupled to the second display, wherein the first processing unit is configured to output first information in the first display, and the second processing circuitry is configured to output information in the second display, wherein the first information and the second information comprise three dimensional information,
wherein the first processing circuitry is configured to:
acquire a sensor signal from the sensor;
generate a synchronization signal based on the sensor signal;
transmit the synchronization signal to the slave unit;
render the first information to be outputted in the first display; and
transmit the first information to the first display to output the first information on the first display, and
wherein the second processing circuitry is further configured to:
receive the synchronization signal from the master unit;
render the second information to be outputted in the second display based on the synchronization signal; and
transmit the second information to the second display to output the second information on the second display, wherein the synchronization signal is transmitted from the master unit to the slave unit within the wearable device, wherein the first information displayed on the first display and the second information displayed on the second display are displaced based on the synchronization signal, and wherein the displacing provides three-dimensional effect viewing in the wearable device.

2. The wearable device of claim 1, wherein the three dimensional information is comprised both in the master unit and in the slave unit.

3. The wearable device of claim 2, wherein the first processing circuitry is further configured to render the three dimensional information from a first angle, wherein the second processing circuitry is further configured to render the three dimensional information from a second angle, and wherein the second angle is distinct from the first angle in order to achieve a stereo effect for a user at the first and second displays.

4. The wearable device of claim 1, wherein the first processing circuitry is further configured to transmit the synchronization signal to the slave unit via a low bandwidth connection.

5. The wearable device of claim 4, wherein the first processing circuitry is further configured to transmit the synchronization signal to the slave unit via a wireless communication interface.

6. The wearable device of claim 4, wherein the first processing circuitry is further configured to transmit the synchronization signal to the slave unit via a wired communication interface.

7. The wearable device of claim 1, wherein the first processing circuitry is further configured to generate and transmit the synchronization signal based on the sensor signal, and wherein the synchronization signal comprises a global time reference and sensor data.

8. The wearable device of claim 1, wherein the sensor comprises at least one of a gyroscope, an accelerometer, or a magnetometer.

9. The wearable device of claim 1, comprises a second slave unit, wherein each of the slave unit and the second slave unit comprises a corresponding display and a corresponding processing circuitry.

10. The wearable device of claim 1, wherein the master unit further comprises a first memory, and wherein the slave unit further comprises a second memory.

11. The wearable device of claim 1, wherein the wearable device further comprises a pair of eyeglasses.

12. The wearable device of claim 1, wherein the wearable device further comprises a headgear, and wherein the first display and the second display are arranged in respective eye positions of a user.

13. The wearable device claim 1, wherein the first information and the second information comprise either augmented reality or virtual reality.

14. A method, implemented by a wearable device, wherein the wearable device comprises a master unit and a slave unit, wherein the master unit comprises a first display and a first processing circuitry coupled to the first display, wherein the slave unit comprises a second display and a second processing circuitry coupled to the second display, and wherein the method comprises:
acquiring, by the first processing circuitry, a sensor signal from a sensor comprised in the master unit and coupled to the first processing circuitry;
generating, by the first processing circuitry, a synchronization signal based on the sensor signal;
transmitting the synchronization signal from the first processing circuitry to the second processing circuitry;
rendering information to output in the first display and in the second display based on the synchronization signal; and
outputting the information on the first display and the second display, respectively, according to the synchronization signal, wherein the synchronization signal is transmitted from the master unit to the slave unit within the wearable device, wherein the first information outputted on the first display and the second information outputted on the second display are displaced based on the synchronization signal, and wherein the displacing provides three-dimensional effect viewing in the wearable device.

15. The method of claim 14, wherein the three dimensional information is comprised in the master unit and in the slave unit.

16. The method of claim 15, further comprising:
rendering, by the first processing circuitry, the three dimensional information from a first angle; and
rendering, by the second processing circuitry, the three dimensional information from a second angle, wherein the second angle is distinct from the first angle in order to achieve a stereo effect for a user at the first and second displays.

17. The method of claim 14, wherein the synchronization signal comprises a global time reference, and sensor data, based on the sensor signal.

18. The method of claim 14, wherein the first processing circuitry uses a low bandwidth connection to transmit the synchronization signal to the slave unit.

19. The method of claim 14, wherein the wearable device comprises a pair of eyeglasses.

20. The method of claim 14, wherein the information comprises either augmented reality or virtual reality.

* * * * *